(12) United States Patent
Ghosh et al.

(10) Patent No.: US 8,062,987 B2
(45) Date of Patent: Nov. 22, 2011

(54) PHOSPHORUS-CONTAINING ZEOLITE CATALYSTS AND THEIR METHOD OF PREPARATION

(75) Inventors: Ashim Kumar Ghosh, Houston, TX (US); Neeta Kulkarni, Houston, TX (US); Pamela Harvey, Missouri City, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 12/573,249

(22) Filed: Oct. 5, 2009

(65) Prior Publication Data

US 2011/0082025 A1    Apr. 7, 2011

(51) Int. Cl.
*B01J 29/06* (2006.01)
(52) U.S. Cl. ............... 502/60; 502/63; 502/64; 502/71; 502/77; 502/85
(58) Field of Classification Search ............ 502/60, 502/63, 64, 71, 77, 85
See application file for complete search history.

(56) References Cited

U.S. PATENT DOCUMENTS

| | | |
|---|---|---|
| 3,562,345 A | 2/1971 | Mitsche |
| 3,702,886 A | 11/1972 | Argauer et al. |
| 3,950,242 A | 4/1976 | Garwood et al. |
| 3,962,364 A | 6/1976 | Young |
| 3,965,207 A | 6/1976 | Weinstein |
| 4,002,697 A | 1/1977 | Chen |
| 4,025,606 A | 5/1977 | Acres |
| 4,080,395 A * | 3/1978 | Butter ............... 585/407 |
| 4,080,396 A * | 3/1978 | Butter ............... 585/407 |
| 4,086,287 A * | 4/1978 | Kaeding et al. ......... 585/466 |
| 4,100,215 A | 7/1978 | Chen |
| 4,115,424 A | 9/1978 | Unland et al. |
| 4,140,726 A | 2/1979 | Unland et al. |
| 4,152,364 A | 5/1979 | Chu |
| 4,250,345 A | 2/1981 | Chu |
| 4,278,827 A | 7/1981 | Chu et al. |
| 4,363,750 A | 12/1982 | Rozovsky et al. |
| 4,377,718 A | 3/1983 | Sato et al. |
| 4,380,685 A | 4/1983 | Chu |
| 4,409,132 A | 10/1983 | Forbus et al. |

(Continued)

FOREIGN PATENT DOCUMENTS

JP        61221137 A2    10/1971

OTHER PUBLICATIONS

F.M. Bautista, et al., Toluene Methylation ON AlPO4-Al2O3 Catalysts, React. Kinet. Catal. Lett., 1996, pp. 61-70, vol. 57, No. 1.

(Continued)

*Primary Examiner* — Elizabeth Wood
(74) *Attorney, Agent, or Firm* — Grady K. Bergen; Griggs Bergen LLP

(57) ABSTRACT

A zeolite catalyst that may be used in aromatic alkylation is prepared by treating a zeolite with a phosphorus compound. The phosphorus-treated zeolite is calcined and contacted with liquid water, whereby an amount of phosphorus is removed from the phosphorus-treated zeolite. The phosphorus-treated zeolite is then heated. A method of preparing an aromatic product may also be carried out by contacting the prepared zeolite catalyst with an aromatic alkylation feed of an aromatic compound and an alkylating agent under reaction conditions suitable for aromatic alkylation.

20 Claims, 1 Drawing Sheet

U.S. PATENT DOCUMENTS

| | | | |
|---|---|---|---|
| 4,415,477 A | 11/1983 | Rozovsky et al. | |
| 4,417,076 A | 11/1983 | Rozovsky et al. | |
| 4,444,989 A | 4/1984 | Herkes | |
| RE31,919 E | 6/1985 | Butter et al. | |
| 4,536,375 A | 8/1985 | Holt et al. | |
| 4,548,914 A * | 10/1985 | Chu | 502/85 |
| 4,554,394 A | 11/1985 | Forbus et al. | |
| 4,590,321 A | 5/1986 | Chu | |
| 4,623,530 A | 11/1986 | Cullo et al. | |
| 4,623,633 A | 11/1986 | Young | |
| 4,638,106 A | 1/1987 | Pieters et al. | |
| 4,657,884 A | 4/1987 | Luft et al. | |
| 4,665,251 A | 5/1987 | Chu | |
| 4,670,616 A | 6/1987 | De Simone et al. | |
| 4,673,767 A | 6/1987 | Nimry et al. | |
| 4,681,745 A | 7/1987 | Pinto | |
| 4,694,114 A | 9/1987 | Chu et al. | |
| 4,695,442 A | 9/1987 | Pinto et al. | |
| 4,695,666 A | 9/1987 | Chao et al. | |
| 4,695,667 A | 9/1987 | Sumitani et al. | |
| 4,704,495 A | 11/1987 | Dessau | |
| 4,716,135 A | 12/1987 | Chen | |
| 4,721,827 A | 1/1988 | Cullo et al. | |
| 4,727,209 A | 2/1988 | Chao | |
| 4,746,763 A | 5/1988 | Kocal | |
| 4,758,328 A | 7/1988 | Young | |
| 4,761,513 A | 8/1988 | Steacy | |
| 4,781,815 A | 11/1988 | Pellet et al. | |
| 4,847,223 A | 7/1989 | Le Van Mao et al. | |
| 4,861,930 A | 8/1989 | Cottrell et al. | |
| 4,873,067 A | 10/1989 | Valyocsik et al. | |
| 4,891,197 A | 1/1990 | Derouane et al. | |
| 4,891,467 A | 1/1990 | Sikkenga | |
| 4,902,406 A | 2/1990 | Valyocsik | |
| 4,910,007 A | 3/1990 | Pinto et al. | |
| 4,912,073 A | 3/1990 | Chu | |
| 4,914,067 A | 4/1990 | Pellet et al. | |
| 4,935,574 A | 6/1990 | D'Amore et al. | |
| 4,962,255 A | 10/1990 | Fraenkel et al. | |
| 4,973,399 A | 11/1990 | Green et al. | |
| 4,973,781 A | 11/1990 | Valyocsik et al. | |
| 4,980,052 A | 12/1990 | Green et al. | |
| 5,041,402 A | 8/1991 | Casci et al. | |
| 5,043,502 A | 8/1991 | Martindale et al. | |
| 5,047,141 A | 9/1991 | Chu | |
| 5,068,483 A | 11/1991 | Barthomeuf et al. | |
| 5,094,995 A | 3/1992 | Butt et al. | |
| 5,105,047 A | 4/1992 | Waller | |
| 5,108,579 A | 4/1992 | Casci | |
| 5,110,776 A | 5/1992 | Chitnis et al. | |
| 5,124,299 A | 6/1992 | Waller | |
| 5,171,921 A | 12/1992 | Gaffney et al. | |
| 5,173,461 A | 12/1992 | Absil et al. | |
| 5,178,748 A | 1/1993 | Casci et al. | |
| 5,210,356 A | 5/1993 | Shamshoum et al. | |
| 5,227,558 A | 7/1993 | Shamshoum et al. | |
| 5,231,064 A | 7/1993 | Absil et al. | |
| 5,233,102 A | 8/1993 | Butt et al. | |
| 5,246,688 A | 9/1993 | Faust et al. | |
| 5,248,841 A | 9/1993 | Young | |
| 5,254,767 A | 10/1993 | Dwyer | |
| 5,254,770 A | 10/1993 | Olson et al. | |
| 5,294,332 A | 3/1994 | Klotz | |
| 5,294,578 A | 3/1994 | Ho et al. | |
| 5,315,033 A | 5/1994 | Butt et al. | |
| 5,318,696 A | 6/1994 | Kowalski | |
| 5,321,183 A | 6/1994 | Chang et al. | |
| 5,330,732 A | 7/1994 | Ishibashi et al. | |
| 5,336,478 A | 8/1994 | Dwyer et al. | |
| 5,336,824 A | 8/1994 | Shamshoum et al. | |
| 5,345,021 A | 9/1994 | Casci et al. | |
| 5,348,643 A | 9/1994 | Absil et al. | |
| 5,349,113 A | 9/1994 | Chang et al. | |
| 5,365,003 A | 11/1994 | Chang et al. | |
| 5,366,948 A | 11/1994 | Absil et al. | |
| 5,367,100 A | 11/1994 | Gongwei et al. | |
| 5,371,307 A | 12/1994 | Guth et al. | |
| 5,378,670 A | 1/1995 | Kumar | |
| 5,380,690 A | 1/1995 | Zhicheng et al. | |
| 5,385,718 A | 1/1995 | Casci et al. | |
| 5,387,732 A | 2/1995 | Shamshoum et al. | |
| 5,399,336 A | 3/1995 | Guth et al. | |
| 5,430,212 A | 7/1995 | Butt et al. | |
| 5,430,213 A | 7/1995 | Hendriksen et al. | |
| 5,446,234 A | 8/1995 | Casci et al. | |
| 5,455,213 A | 10/1995 | Chang et al. | |
| 5,456,821 A | 10/1995 | Absil et al. | |
| 5,464,799 A | 11/1995 | Casci et al. | |
| 5,475,179 A | 12/1995 | Chang et al. | |
| 5,498,814 A | 3/1996 | Chang et al. | |
| 5,503,818 A | 4/1996 | Nicolaides | |
| 5,512,260 A | 4/1996 | Kiliany et al. | |
| 5,516,736 A | 5/1996 | Chang et al. | |
| 5,523,510 A | 6/1996 | Pellet et al. | |
| 5,529,964 A | 6/1996 | Weitkamp et al. | |
| 5,534,239 A | 7/1996 | Fajula et al. | |
| 5,536,894 A | 7/1996 | Degnan et al. | |
| 5,541,146 A | 7/1996 | Chang et al. | |
| 5,561,095 A | 10/1996 | Chen et al. | |
| 5,563,310 A | 10/1996 | Chang et al. | |
| 5,569,805 A | 10/1996 | Beck et al. | |
| 5,571,768 A * | 11/1996 | Chang et al. | 502/64 |
| 5,573,746 A | 11/1996 | Chen | |
| 5,576,256 A | 11/1996 | Monque et al. | |
| 5,602,066 A * | 2/1997 | Beck et al. | 502/64 |
| 5,607,888 A | 3/1997 | Chang et al. | |
| 5,607,890 A | 3/1997 | Chen et al. | |
| 5,646,314 A | 7/1997 | Crocco et al. | |
| 5,648,580 A | 7/1997 | Chen et al. | |
| 5,658,454 A | 8/1997 | Absil et al. | |
| 5,675,047 A | 10/1997 | Beck et al. | |
| 5,689,024 A | 11/1997 | Schmitt | |
| 5,698,756 A | 12/1997 | Beck et al. | |
| 5,726,114 A * | 3/1998 | Chang et al. | 502/64 |
| 5,780,563 A | 7/1998 | Chen et al. | |
| 5,789,335 A | 8/1998 | Chen et al. | |
| 5,811,613 A | 9/1998 | Bhat et al. | |
| 5,833,840 A | 11/1998 | Absil et al. | |
| 5,847,255 A | 12/1998 | Ghosh et al. | |
| 5,856,603 A | 1/1999 | Rekker et al. | |
| 5,902,919 A | 5/1999 | Chen et al. | |
| 5,905,051 A | 5/1999 | Wu et al. | |
| 5,907,073 A | 5/1999 | Ghosh | |
| 5,922,922 A | 7/1999 | Harris et al. | |
| 5,925,586 A | 7/1999 | Sun | |
| 5,939,597 A | 8/1999 | Dessau et al. | |
| 5,951,963 A | 9/1999 | He et al. | |
| 5,952,535 A | 9/1999 | King et al. | |
| 5,955,641 A | 9/1999 | Chen et al. | |
| 5,968,463 A | 10/1999 | Shelef et al. | |
| 5,990,031 A | 11/1999 | Ghosh | |
| 5,994,603 A | 11/1999 | Mohr et al. | |
| 6,034,283 A | 3/2000 | Ban et al. | |
| 6,040,257 A | 3/2000 | Drake et al. | |
| 6,046,128 A | 4/2000 | Kisen et al. | |
| 6,047,544 A | 4/2000 | Yamamoto et al. | |
| 6,048,816 A | 4/2000 | Brown et al. | |
| 6,057,485 A | 5/2000 | Merrill et al. | |
| 6,060,633 A | 5/2000 | Chen et al. | |
| 6,074,975 A | 6/2000 | Yao et al. | |
| 6,080,303 A | 6/2000 | Cao et al. | |
| 6,080,698 A | 6/2000 | Zhang et al. | |
| 6,083,865 A | 7/2000 | Drake et al. | |
| 6,090,274 A | 7/2000 | Wu et al. | |
| 6,090,991 A | 7/2000 | Butler et al. | |
| 6,096,938 A | 8/2000 | Ghosh | |
| 6,100,437 A | 8/2000 | Koehl et al. | |
| 6,124,227 A | 9/2000 | Yao et al. | |
| 6,150,293 A | 11/2000 | Verduijn et al. | |
| 6,156,949 A | 12/2000 | Brown et al. | |
| 6,160,191 A | 12/2000 | Smith et al. | |
| 6,187,982 B1 | 2/2001 | Beck et al. | |
| 6,211,104 B1 | 4/2001 | Shi et al. | |
| 6,217,748 B1 | 4/2001 | Hatanaka et al. | |
| 6,222,084 B1 | 4/2001 | Ghosh et al. | |
| 6,251,263 B1 | 6/2001 | Hatanaka et al. | |
| 6,268,305 B1 | 7/2001 | Butler et al. | |

| | | |
|---|---|---|
| 6,294,493 B1 | 9/2001 | Strohmaier et al. |
| 6,300,535 B1 | 10/2001 | van den Berge et al. |
| 6,306,790 B1 | 10/2001 | Rodriguez et al. |
| 6,319,484 B1 | 11/2001 | Shore et al. |
| 6,342,153 B1 | 1/2002 | Guan et al. |
| 6,346,190 B1 | 2/2002 | Khare |
| 6,388,156 B1 | 5/2002 | Ou et al. |
| 6,395,664 B1 | 5/2002 | Boehner et al. |
| 6,399,530 B1 | 6/2002 | Chen et al. |
| 6,417,421 B1 | 7/2002 | Yao |
| 6,423,879 B1 | 7/2002 | Brown et al. |
| 6,444,610 B1 | 9/2002 | Yamamoto |
| 6,459,006 B1 | 10/2002 | Ou et al. |
| 6,469,095 B1 | 10/2002 | Gareiss et al. |
| 6,503,862 B1 | 1/2003 | Yamamoto |
| 6,504,072 B1 | 1/2003 | Brown et al. |
| 6,504,074 B2 | 1/2003 | Berduijn et al. |
| 6,506,954 B1 | 1/2003 | Brown et al. |
| 6,518,213 B1 | 2/2003 | Yamamoto et al. |
| 6,548,725 B2 | 4/2003 | Froment et al. |
| 6,566,293 B1 | 5/2003 | Vogt et al. |
| 6,576,582 B1 * | 6/2003 | Beck et al. ............... 502/71 |
| 6,589,901 B2 | 7/2003 | Yamamoto |
| 6,613,708 B1 | 9/2003 | Ou et al. |
| 6,613,951 B1 | 9/2003 | Brown et al. |
| 6,642,426 B1 | 11/2003 | Johnson et al. |
| 6,689,929 B2 | 2/2004 | Williams et al. |
| 6,699,811 B1 | 3/2004 | Mohr et al. |
| 6,723,297 B2 | 4/2004 | Chen et al. |
| 6,726,834 B2 | 4/2004 | Quesada et al. |
| 6,770,251 B2 | 8/2004 | Yoshikawa |
| 6,773,694 B1 | 8/2004 | Lesch et al. |
| 6,799,089 B2 | 9/2004 | Toulhoat |
| 6,811,684 B2 | 11/2004 | Mohr et al. |
| 6,812,181 B2 | 11/2004 | van der Berge et al. |
| 6,864,399 B2 | 3/2005 | Merrill et al. |
| 6,943,131 B1 | 9/2005 | Ghosh et al. |
| 7,060,644 B2 | 6/2006 | Ghosh et al. |
| 7,060,864 B2 | 6/2006 | Ghosh et al. |
| 7,084,318 B2 | 8/2006 | Ghosh et al. |
| 7,105,713 B2 | 9/2006 | Ghosh et al. |
| 7,119,239 B2 | 10/2006 | Johnson et al. |
| 7,176,339 B2 | 2/2007 | Iaccino et al. |
| 7,186,873 B2 | 3/2007 | Feng et al. |
| 7,196,237 B2 | 3/2007 | Ghosh et al. |
| 7,232,516 B2 | 6/2007 | Sughure, II. et al. |
| 7,279,608 B2 | 10/2007 | Ghosh et al. |
| 7,285,511 B2 | 10/2007 | Ghosh et al. |
| 7,304,194 B2 | 12/2007 | Ghosh et al. |
| 7,363,410 B2 | 4/2008 | Bian et al. |
| 7,368,410 B2 | 5/2008 | Ghosh et al. |
| 7,396,967 B2 | 7/2008 | Iaccino et al. |
| 7,399,727 B2 | 7/2008 | Ghosh et al. |
| 7,446,069 B2 | 11/2008 | Ghosh et al. |
| 7,662,737 B2 | 2/2010 | Ghosh et al. |
| 2003/0004383 A1 | 1/2003 | Brown et al. |
| 2003/0055305 A1 * | 3/2003 | Beck et al. ............... 585/643 |
| 2003/0121827 A1 | 7/2003 | van den Berge et al. |
| 2003/0127360 A1 | 7/2003 | van den Berge et al. |
| 2004/0004023 A1 | 1/2004 | Sughrue, II et al. |
| 2004/0087822 A1 | 5/2004 | Buchanan et al. |
| 2004/0158111 A1 | 8/2004 | Johnson et al. |
| 2004/0262200 A1 | 12/2004 | Sughrue, II et al. |
| 2005/0020435 A1 | 1/2005 | Beck et al. |
| 2005/0070749 A1 | 3/2005 | Ghosh et al. |
| 2005/0075524 A1 | 4/2005 | Feng et al. |
| 2005/0143613 A1 | 6/2005 | Dakka et al. |
| 2005/0194289 A1 | 9/2005 | Overbeek et al. |
| 2005/0202956 A1 | 9/2005 | Sterte et al. |
| 2006/0151358 A1 | 7/2006 | Brown et al. |
| 2007/0015658 A1 | 1/2007 | Turaga et al. |
| 2007/0032374 A1 * | 2/2007 | Lau et al. ............... 502/60 |
| 2007/0149384 A1 * | 6/2007 | Ghosh et al. ............... 502/60 |
| 2007/0225156 A1 | 9/2007 | Sughure, II et al. |
| 2008/0058564 A1 | 3/2008 | Iaccino et al. |
| 2009/0253949 A1 | 10/2009 | Ghosh et al. |
| 2010/0113850 A1 | 5/2010 | Ghosh et al. |
| 2010/0168489 A1 | 7/2010 | Ghosh et al. |

OTHER PUBLICATIONS

Oyvind Mikkelsen, et al., Use of Isotopic Labeling for Mechanistic Studies of the Methanol-to-Hydrocarbons reaction. Methylation of toluene with Methanol Over H-ZSM-5, H-Mordenite and H-Beta, Microporous and Mesoporous, Materials, 2000, pp. 93-113, vol. 40.

P.G. Smirniotis, et al., Alkylation of Berizene or Toluene with MeOH or C2H4 over ZSM-5 or B-Zeollte: Effect of the Zeolite Pore Openings and of Hydrocarbons Involved on the Mechanism of Alkylation, Ind. Eng. Chem. Res., 1995, pp. 1517-1528, vol. 34.

F.M. Bautista, et al., Continuous Flow Toluene Methylation Over AlPO4 and AlPO4-Al2O3 Catalysts, Catalysis Letters, 1994, pp. 159-167, vol. 26.

* cited by examiner

PHOSPHORUS-CONTAINING ZEOLITE CATALYSTS AND THEIR METHOD OF PREPARATION

TECHNICAL FIELD

The invention relates generally to catalysts used in aromatic alkylation.

BACKGROUND

Aromatic compounds may be alkylated to form different alkylated aromatic products. One that has particular value is para-xylene. Para-xylene is a valuable substituted aromatic compound because of the great demand for its oxidation to terephthalic acid, a major component in forming polyester fibers and resins. It can be commercially produced from hydrotreating of naphtha (catalytic reforming), steam cracking of naphtha or gas oil, and toluene disproportionation.

Alkylation of toluene with methanol, which is also known as toluene methylation, has been used in laboratory studies to produce para-xylene. Toluene methylation has been known to occur over acidic catalyst, particularly over zeolite or zeolite-type catalyst. In particular, ZSM-5 zeolite, zeolite Beta and silicaaluminophosphate (SAPO) catalysts have been used for this process. Generally, a thermodynamic equilibrium mixture of ortho (o)-, meta (m)- and para (p)-xylenes can be formed from the methylation of toluene, as is illustrated by the reaction below.

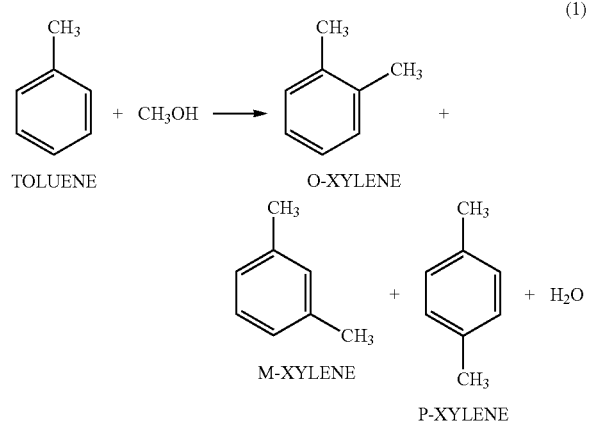

(1)

Thermodynamic equilibrium compositions of o-, m-, and p-xylenes may be around 25, 50 and 25 mole %, respectively, at a reaction temperature of about 500° C. Such toluene methylation may occur over a wide range of temperatures, however. Byproducts such as C9+ and other aromatic products can be produced by secondary alkylation of the xylene product.

Para-xylene can be separated from mixed xylenes by a cycle of adsorption and isomerization. Such cycle may have to be repeated several times because of the low isomeric concentration in the equilibrium mixture. A high purity grade (99+%) p-xylene is desirable for its oxidation to terephthalic acid. The production cost for such a high purity grade p-xylene can be very high, however. A different method that employs crystallization techniques can be used and may be less expensive where the concentration of p-xylene is around 80% or higher in the initial xylene product. Thus, higher than equilibrium concentrations of p-xylene may be desirable.

A significantly higher amount of p-xylene can be obtained in toluene methylation reactions if the catalyst has shape selective properties. Shape selective properties can be obtained in modified zeolite catalysts by narrowing the size of the zeolite pore openings, inactivation of the external surface of the zeolite or controlling zeolite acidity. Toluene methylation may occur over modified ZSM-5 zeolite catalysts giving xylene products containing significantly greater amounts of p-xylene than the thermodynamic concentration.

The present invention is directed to a catalyst and a method of preparation of a catalyst that has shape selective properties and that also has increased catalyst stability when used in aromatic alkylation reactions, such a toluene methylation.

BRIEF DESCRIPTION OF THE DRAWINGS

For a more complete understanding of the present invention, reference is now made to the following descriptions taken in conjunction with the accompanying figures, in which.

DETAILED DESCRIPTION

Figure 1:
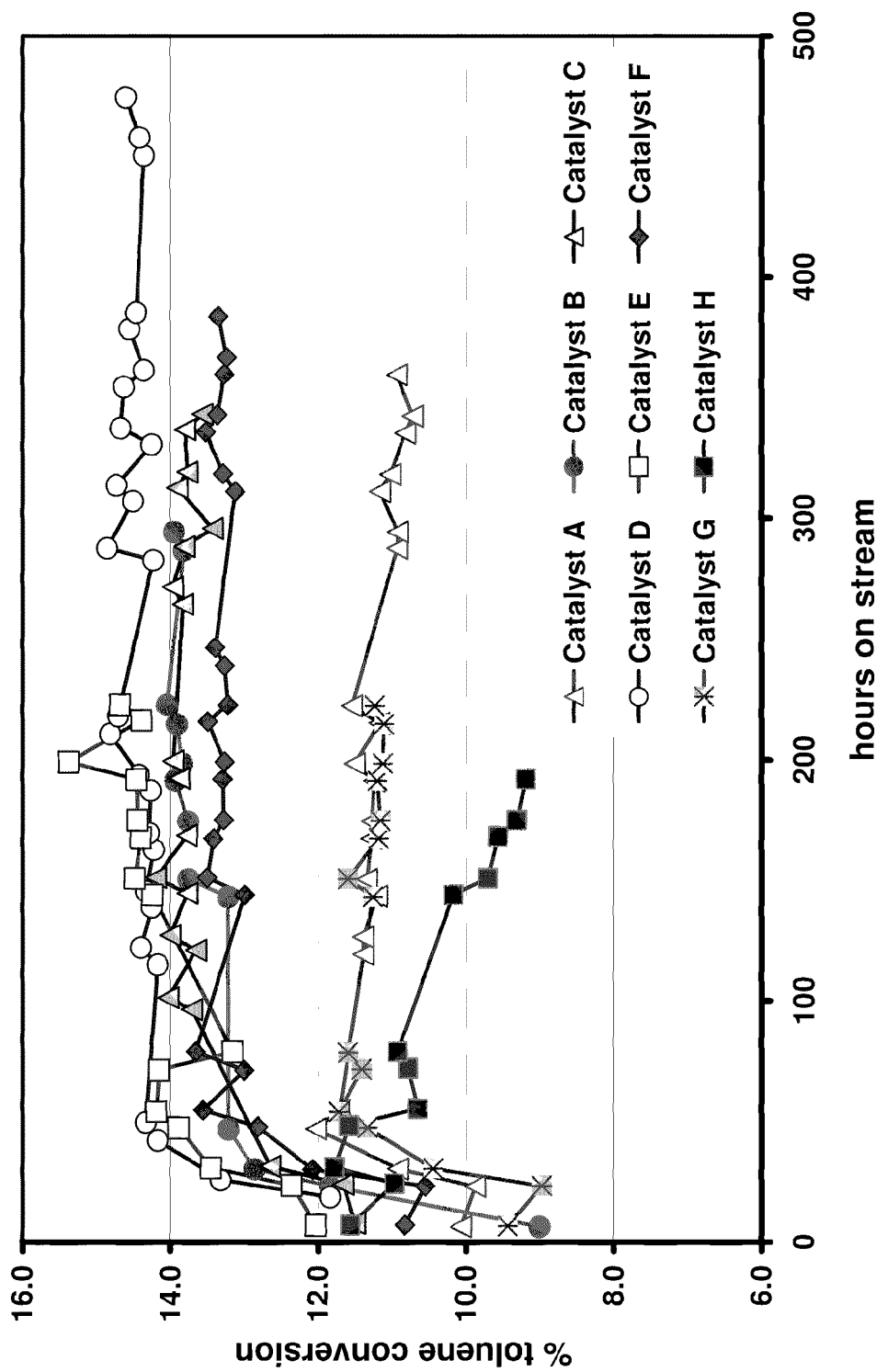
FIG. 1 shows a plot of toluene conversion over time for toluene methylation reactions using phosphorus-treated ZSM-5 zeolite catalysts (Catalyst A-H) of which some have undergone a liquid water pretreatment and others have undergone either no water pretreatment or a vapor water pretreatment.

Zeolites are aluminosilicate materials having microporous structures. They may be naturally occurring or synthesized. Zeolites are commonly used as catalysts in a variety of different hydrocarbon conversion reactions such as isomerization and alkylation reactions. Among these is the alkylation of aromatic compounds.

The ZSM-5 zeolite is one of the most versatile zeolites used for catalyst in aromatic alkylation. Specific reference is made to the use of a ZSM-5 zeolite that has been modified in accordance with the invention for use in toluene methylation, for which the modified zeolite is particularly well suited. The invention has application to other zeolites, however, particularly those of medium pore size, which are those having an average pore size of from about 5.0 Å to about 7.0 Å. The ZSM-5 zeolite has an average pore diameter of from about 5.1 Å to about 5.6 Å. Non-limiting examples of medium pore zeolites include ZSM-5, omega and mordenite zeolites. It will also be apparent to those skilled in the art that although the zeolite catalysts described herein are used in toluene methylation, they may have application for use in other types of reactions, such as transalkylation and other aromatic alkylation reactions. In particular, the catalyst of the invention may have application to reactions to provide increased selectivity for para-isomers in mixed dialkylated aromatic products.

ZSM-5 zeolites and their preparation are described in U.S. Pat. No. 3,702,886, which is herein incorporated by reference. The starting ZSM-5 zeolite may be an $NH_4^+$ or $H^+$ form and may contain traces of other cations. In the present invention, the starting ZSM-5 zeolite may have a silica/alumina molar ratio of from about 30 or lower to about 1000 or higher prior to modification, more particularly, the silica/alumina molar ratio may be from about 30, 50, 80, 100, 200, 250, 280, 300, 350, 400, 500 to about 1000 or more, including any and all data points within such range and the end points of such range. In certain applications, the ZSM-5 zeolite may have a silica/alumina molar ratio of from about 250 or more, and still more particularly from about 280 to about 1000 or more, prior to modification.

It should be understood that with respect to any concentration or amount range listed or described herein as being useful, suitable, or the like, it is intended to include every concentration or amount within the range, including the end points, and is to be considered as having been specifically stated. For example, "a range of from 1 to 10" is to be read as indicating each and every possible number along the continuum between about 1 and about 10. Thus, even if specific data points within the range, or even no data points within the range, are explicitly identified or refer to only a specific few, it is to be understood that the inventors appreciate and understand that any and all data points within the range are to be considered to have been specified, and that the inventors are in possession of the entire range and all points within the range.

To provide para-selective properties to the ZSM-5 zeolite or other zeolites, the zeolite is modified by treating it with phosphorus-containing compounds. Such phosphorus-containing compounds may include, but are not limited to, phosphonic, phosphinous, phosphorus and phosphoric acids, salts and esters of such acids and phosphorous halides. In particular, phosphoric acid ($H_3PO_4$) and ammonium hydrogen phosphate (($NH_4$)$_2HPO_4$) may be used as the phosphorus-containing compound to provide a catalyst for aromatic alkylation or toluene methylation with shape selective properties to provide increased para-selectivity. Such modified catalysts may contain phosphorus (P) in an amount of from about 0.01 wt % to about 15 wt % or more by weight of the zeolite. In certain embodiments, the phosphorus content may be from about 8 wt % or 9 wt % or more by weight of the zeolite.

The phosphorus treatment may be carried out by various techniques. This may include aqueous phosphorus treatment of the zeolite. The treatment may include slurry evaporation, wet incipient and spray-dry methods. Solid-solid mixing of the zeolite and a phosphorus compound followed by bringing the mixture in contact with water as a liquid or vapor phase may also be used.

In slurry evaporation, the phosphorus may be incorporated into the catalyst by preparing a slurry of the zeolite and an aqueous solution of the phosphorus compound. Heating of the slurry may be used to facilitate treatment of the zeolite and to evaporate liquids. Heating of the slurry to temperatures of from about 25° C. or more, with from about 70° C. to about 100° C. may be suitable in most instances. The slurry may also be stirred or agitated during this step to ensure uniform treatment. Heating the zeolite slurry to near complete evaporation of the liquid causes the formation of dough which can be dried or calcined to form powder or particles. The evaporation of the liquid from the zeolite slurry can be alternatively achieved by using a spray-dry technique which is well known in the art.

In the wet incipient method, an aqueous solution of the phosphorus compound is added, such as by spraying, to dry zeolite without forming a slurry. The dry zeolite, which may be initially in the form of a powder, may be mixed with the phosphorus compound or its aqueous solution. If necessary, water may be added to the mixture of zeolite powder and phosphorus containing compound or its solution to facilitate interaction between them.

The phosphorus-treated zeolite is then calcined at a temperature of about 250° C. or more, more particularly, a temperature from about 300° C. to about 700° C., more particularly from about 400° C. to about 570° C., in an environment containing oxygen, typically air. Calcining may take place over time, typically from several minutes to one hour or more. Calcining may also take place by gradually increasing the temperature over time.

The phosphorus-treated ZSM-5 zeolite may provide a treated zeolite with a total pore volume of from about 0.2 ml/g or less. More particularly, the total pore volume may range from about 0.07 ml/g to about 0.18 ml/g, more particularly from about 0.11 ml/g to about 0.15 ml/g. The BET surface area of the phosphorus-treated ZSM-5 zeolite may range from about 10 $m^2$/g to about 300 $m^2$/g, more particularly from about 150 $m^2$/g to about 250 $m^2$/g.

After phosphorus treatment and calcining, the phosphorus-treated zeolite may be optionally bound with a binder. The binder materials may include inorganic oxide materials, such as alumina, clay and silica materials. The binder may be used to provide a desired shape to the catalyst, for example, 1/16-inch cylindrical shaped extruded catalyst. In particular, a binder of an aluminum-containing material, such as alumina, clay, aluminum phosphate, silica-alumina or other-aluminum containing material, or their combinations, may be particularly useful. The bound catalyst may contain from about 1 wt % to about 99 wt % of binder material by total weight of the catalyst. In some applications the binder may be present in an amount of from about 10 wt % to about 50 wt % binder by total weight of catalyst.

In certain embodiments, the P-treated zeolite may be calcined at a temperature of about 300° C. or higher prior to binding and then the zeolite may be bound with a suitable binder, and then calcined again, as described in U.S. Pat. No. 7,368,410, which is herein incorporated by reference.

In some embodiments, even without a binder, the phosphorus-treated zeolite (prior to calcination) can also be formed into a particular shape and size to form a catalyst, for example, 1/16-inch cylindrical shaped extrudates. Such catalyst may be described as "self-bound" catalyst.

The phosphorus-treated and calcined zeolite (either unbound, self-bound or bound with a binder such as alumina) is then treated with a liquid water treatment. This is accomplished by contacting the phosphorus-treated zeolite with liquid water using various methods. As used herein, the expression "liquid water" is meant to encompass water that is primarily in the liquid phase and at conditions that are at or above the water's freezing point and at or below the water's boiling point. In most instances, the liquid water treatment is conducted at a temperature of above 0° C. and below 100° C. with the pressure conditions being at or around atmospheric pressure conditions. There may be other instances, however, where the pressure is below or above atmospheric pressure. In such instances, the liquid water treatment is conducted at a temperature to ensure that the water temperature is at or above the water's freezing point and at or below the boiling point for the particular pressure conditions to ensure that the water is primarily in the liquid phase. In many applications, the liquid water treatment is carried out at a temperature of about 25° C. (room temperature) to about 100° C.

In one method, the liquid water treatment is carried out by immersing the phosphorus-treated zeolite in a liquid water bath. The immersion time may vary from a few minutes to several hours or even days. In most embodiments, the immersion time will range from about 1 hour to 24 hours or more. The immersion may be carried out with or without agitation of the zeolite within the bath.

In another method, the phosphorus-treated zeolite is contacted in a flowing liquid water stream. This may be done by immersing the zeolite in a forced stream of liquid water without the use of any gas diluent. The duration of the flowing liquid stream may range from a few minutes to several hours or even days. The duration times for the flowing liquid stream without the use of any gas diluents may be the same as those for the water bath or may be shorter.

Alternatively, the liquid water may be mixed or entrained within a gas diluent. The gas diluent may be hydrogen gas or other gas (e.g. $N_2$, $CO_2$, light alkanes, air, etc.), which may be inert gases, or combination of such gases. Such treatment may be carried out by bubbling or passing flowing hydrogen or other gas through the liquid water at conditions above the water's freezing point and below the water's boiling point so that some amount of the liquid water is entrained within the flowing gas diluent. The phosphorus-containing zeolite is then contacted with the flowing liquid water/gas mixture. The duration of the flowing liquid water stream entrained within the gas may range from a few minutes to several hours or even days.

After the liquid water treatment, any residual liquid water may be separated from the zeolite, such as through filtration, decantation, etc. Further heating to dry the zeolite after the liquid water treatment may also be carried out. Typical drying temperatures may range from about 70° C. to 100° C. and higher.

The liquid water treatment of the phosphorus-containing zeolite may remove loosely bound phosphorus. As much as 20% or more of the initial phosphorus content may be removed by the liquid water treatment. In some embodiments, from about 20% to about 30% of the initial phosphorus content may be removed by the liquid water treatment.

An additional calcination step may also be employed after the liquid water treatment using the calcination temperatures and times previously discussed.

The zeolite may also undergo a further steaming step, as are many zeolite catalysts, prior to the initial use of the fresh zeolite catalyst. The catalyst may be steamed at a temperature of 300° C. or lower before using the catalyst in any reaction. The steaming can be carried out in-situ or ex-situ of the reactor. In some embodiments, the catalyst is steamed at mild temperatures. Methods for steaming at mild temperatures that are useful in the present invention are described in U.S. Pat. No. 7,304,194, which is herein incorporated by reference. In other embodiments no further steaming may be conducted after the liquid water treatment.

After drying and/or calcinations and any further steam treatment, the liquid-water-treated, phosphorus-containing zeolite may be used as a catalyst in aromatic alkylation reactions. Examples of alkylation reactions for which the invention has application include toluene alkylation with an alkylating agent (e.g. methanol). Other reactions may include aromatic alkylation and transalkylation. While the invention has application to many aromatic alkylation reactions, the zeolite catalyst is particularly well suited for toluene methylation to produce para-xylene using ZSM-5 zeolite catalyst. Although much of the description herein may be directed to such toluene methylation, it will be readily understood by those skilled in the art that it is not solely limited to such use.

The liquid-water-treated, phosphorus-containing zeolite catalyst may be contacted with an appropriate feed of an aromatic hydrocarbon and an alkylating agent under suitable alkylation reaction conditions to carry out aromatic alkylation. In aromatic alkylation an alkylation feed may be used. A gas cofeed may also be used. The cofeed gas may include hydrogen or an inert gas. As used herein, the expression "alkylation feed" is meant to encompass the aromatic compound and the alkylating agent. As used herein with respect to toluene methylation, the expression "methylation feed" is meant to encompass the feed of toluene and methanol.

In addition to any cofeed gas, water that may be in the form of steam, may also be introduced into the reactor as cofeed along with the alkylation feed. The water or steam used for the alkylation or methylation reaction may be introduced, with or without hydrogen or inert gas as cofeed, with the alkylation feed to the reactor during the start up of the alkylation reaction, or it may be introduced subsequent to initial start up. In either case, liquid water may be added and vaporized prior to its mixing with cofeed gas (if any) and the alkylation feed. The use of water cofeed in aromatic alkylation is described in U.S. Pat. No. 7,060,864, which is hereby incorporated by reference. In other applications, no water cofeed may be used.

The reactor pressure for toluene methylation or other aromatic alkylation may vary, but typically ranges from about 10 to about 1000 psig. Reactor temperatures may vary, but typically range from about 400 to about 700° C. Upon introduction of feed into the reactor, the catalyst bed temperature may be adjusted to a selected reaction temperature to effect a desired conversion. The temperature may be increased gradually at a rate of from about 0.1° C./min to about 10° C./min to provide the desired final reactor temperature. As used in the examples, reactor temperature refers to the temperature as measured at the inlet of catalyst bed of the reactor.

The reaction may be carried out in a variety of different reactors that are commonly used for carrying out aromatic alkylation reactions. Single or multiple reactors in series and/or parallel may be suitable for carrying out the aromatic alkylation or toluene methylation reactions.

As used herein, catalytic activity can be expressed as the % moles of the hydrocarbon or reactant converted with respect to the moles of hydrocarbon or reactant fed. In toluene methylation where toluene is converted to xylenes, the catalytic activity may be measured by the toluene converted with respect to the moles of toluene fed and can be defined by the following formulas:

$$\text{Mole \% Toluene Conversion} = [T_i - T_o)/T_i] \times 100 \quad (2)$$

where, $T_i$ is the number of moles of toluene fed and $T_o$ is the number of moles toluene unreacted.

As used herein, selectivity for mixed xylenes may be expressed as:

$$\text{Mole \% Mixed Xylene Selectivity} = [X_{tx}/(T_i - T_o)] \times 100 \quad (3)$$

where, $X_{tx}$ is the number of moles of total or mixed (o-, m- or p-) xylenes in the product.

As used herein, selectivity for p-xylene may be expressed as:

$$\text{Mole \% p-Xylene Selectivity} = (X_p/X_{tx}) \times 100 \quad (4)$$

where, $X_p$ is the number of moles of p-xylene.

As used herein, methanol conversion may be expressed as:

$$\text{Mole \% Methanol Conversion} = [(M_i - M_o)/M_i] \times 100 \quad (5)$$

where, $M_i$ is the number of moles of methanol fed and $M_o$ is the number of moles methanol unreacted.

As used herein, methanol selectivity for toluene methylation may be expressed as:

$$\text{Mole \% Methanol Selectivity} = [X_{tx}/(M_i - M_o)] \times 100 \quad (6)$$

where, $X_{tx}$ is the number of moles of mixed (o-, m- or p-) xylenes, $M_i$ is the number of moles of methanol fed and $M_o$ is the number of moles of unreacted methanol.

The following examples better serve to illustrate the invention.

EXAMPLES

Example 1

Comparative Catalyst A

A $NH_4$-ZSM-5 zeolite powder having a $SiO_2/Al_2O_3$ mole ratio of about 280 was treated with aqueous $H_3PO_4$ and then was calcined at a temperature of about 530° C. The phosphorus treated ZSM-5 zeolite was crushed into fine powder and was then combined with about 20% by weight of alumina binder and extruded into 1/16-inch diameter cylindrical-shaped extrudates. The bound zeolite extrudates were then calcined or heated to a temperature of 530° C. to form a base catalyst (Catalyst A) that contained approximately 7.5 wt % phosphorus by total weight of catalyst. Catalyst A was then used (Examples 2 and 3) to evaluate the effect of different liquid water treatments on the performance a phosphorus-treated zeolite catalyst.

Example 2

Catalyst B

About 30.1 g of Catalyst A was immersed in 100 ml water in a flask (mouth covered with aluminum foil) and placed in an oven overnight at a temperature of about 60° C. Catalyst was separated by decanting the water and was dried and calcined for 10 hours at a temperature of about 530° C. to form Catalyst B.

Example 3

Catalyst C

About 5.1 g of Catalyst A was placed in a reactor tube and was treated by flowing water. The water was fed at 1.0 ml/min along with $H_2$ gas at 458 cc/min through the catalyst bed at room temperature for about 5 hours. The catalyst was then calcined for 10 hours at a temperature of about 530° C. to form Catalyst C.

Catalyst D

About 2.5 g of Catalyst A was placed in a reactor tube and was treated by flowing water. The water was fed at 1.0 ml/min along with $H_2$ gas at 458 cc/min through the catalyst bed at about 60° C. for about 5 hours. The water treatment of Catalyst A was repeated with another fresh catalyst load (2.5 g), and the two loads were then mixed together and calcined for 10 hours at a temperature of about 530° C. to form Catalyst D.

Catalyst E

About 2.5 g of Catalyst A was placed in a reactor tube and was treated by flowing water. The water was fed at 1.0 ml/min along with $H_2$ gas at 458 cc/min through the catalyst bed at about 100° C. for about 5 hours. The water treatment of Catalyst A was repeated with another fresh catalyst load (2.5 g) and the two loads were then mixed together and calcined for 10 hours at a temperature of about 540° C. to form Catalyst E.

Catalyst F

About 3.0 g of Catalyst A was placed in a reactor tube and was treated by flowing water. The water was fed at 1.0 ml/min along with $H_2$ gas at 458 cc/min through the catalyst bed at about 350° C. for about 5 hours. The water treatment of Catalyst A was repeated with another fresh catalyst load (3.0 g) and the two loads were then mixed together and calcined for 10 hours at a temperature of about 540° C. to form Catalyst F.

Catalyst G

About 3.0 g of Catalyst A was placed in a reactor tube and was treated by flowing water. The water was fed at 1.0 ml/min along with $H_2$ gas at 458 cc/min through the catalyst bed at about 500° C. for about 5 hours. The water treatment of Catalyst A was repeated with another fresh catalyst load (3.0 g) and the two loads were then mixed together and calcined for 10 hours at a temperature of about 540° C. to form Catalyst G.

The water treatment of Catalyst A to make Catalysts B-G are summarized in Table 1.

TABLE 1

P/ZSM-5 Catalyst Treated with Water

| Catalyst # | Conditions for Water Treatment |
|---|---|
| A | P-modified ZSM-5, alumina bound and extruded and calcined. No water treatment |
| B | Immersed Catalyst A in water at 60° C. overnight, catalyst separated from water, and calcined at 530° C. 10 h |
| C | Water (+$H_2$) fed through catalyst bed (Catalyst A) at room temperature for 5 h, calcined at 530° C. 10 h |
| D | Water (+$H_2$) fed through catalyst bed (Catalyst A) at 60° C. for 5 h, calcined at 530° C. 10 h |
| E | Water (+$H_2$) fed through catalyst bed (Catalyst A) at 100° C. for 5 h, calcined at 540° C. 10 h |
| F | Water (+$H_2$) fed through catalyst bed (Catalyst A) at 350° C. for 5 h, calcined at 540° C. 10 h |
| G | Water (+H2) fed through catalyst bed (Catalyst A) at 500° C. for 5 h, calcined at 540° C. 10 h |
| H | P-modified ZSM-5, alumina bound and extruded and calcined. % P lower than Catalyst A |

Example 4

Each of the Catalysts A-G described above were used in toluene methylation reactions. In each case, a fresh load of 5.4 ml of catalyst was loaded in a reactor. The catalyst was further dried by slowly raising the catalyst bed temperature at about 5° C./min to 480° C. under hydrogen flow (50 cc/min) for at least 2 hours. The catalyst was then steamed by introducing water vapor (2.2 mmole/min) with a carrier gas of $H_2$ (459 cc/min) at 200° C. overnight. A premixed toluene and methanol feed (molar ratio 4.5) was added to the reactor at 200° C. and the catalyst bed inlet temperature was slowly increased to 485° C. The liquid hourly space velocity (LHSV) based on methylation feed (toluene+methanol) was maintained at about 2 $hr^{-1}$ and a cofeed $H_2$ gas was fed and maintained to provide a $H_2$/methylation feed molar feed ratio of about 7-8. In addition, water was added to the reactor as cofeed and was vaporized prior to introduction to the reactor. The $H_2O$/methylation feed molar ratio was about 0.8 and the reactor pressure was about 20 psig. Reactor streams were analyzed to calculate conversion and selectivity. The results are present in FIG. 1.

As shown in FIG. 1, the non-water-treated phosphorus-containing zeolite (Catalyst A) showed about 11.5 mole % toluene conversion under the conditions used and the conversion slowly declined with time on stream. The phosphorus-treated zeolite when treated with flowing liquid water through the catalyst bed at room temperature (Catalyst C), at 60° C. (Catalyst D) and at 100° C. (Catalyst E), or by immersing the catalyst in water at 60° C. (Catalyst B) showed significantly higher toluene conversion of about 14 mole %. There was also no apparent decline in conversion with time on stream for these catalysts. When the phosphorus-containing ZSM-5 zeolite was treated with water vapor above its boiling point, for example 500° C. (Catalyst G), the pretreated catalyst showed no improved activity and showed the same deactivation profile as the untreated catalyst (Catalyst A).

Referring to Table 2 below, each of the water pretreated catalysts (Catalysts B-G) showed lower amounts of phosphorus content compared to the non-water-treated catalyst (Catalyst A). This suggests that the water removed loosely bound phosphorus or the phosphorus may occlude the zeolite pores/channels.

TABLE 2

P/ZSM-5 Catalyst Treated with Water

| Catalyst | Catalyst Description | P, wt % | % P Removed* | SA, m2/g | PV, ml/g |
|---|---|---|---|---|---|
| A | P-Modified ZSM-5, Alumina bound and extruded and calcined. No water treatment. | 7.5 | N/A | 205 | 0.162 |
| B | Immersed Catalyst A in water at 60° C. overnight, filtered to remove water, and calcined. | 5.41 | 27.87 | 209 | 0.177 |
| C | Water (+H2) fed through bed of Catalyst A at room temperature for 5 h, and calcined. | 5.18 | 22.93 | 193 | 0.140 |
| D | Water (+H2) fed through bed of Catalyst A at 60° C. for 5 h, and calcined. | 5.86 | 21.87 | 189 | 0.139 |
| E | Water (+H2) fed through bed of Catalyst A at 100° C. for 5 h, and calcined. | 5.58 | 25.60 | 196 | 0.158 |
| F | Water (+H2) fed through bed of Catalyst A at 350° C. for 5 h, and calcined. | 6.44 | 14.13 | 167 | 0.132 |
| G | Water (+H2) fed through bed of Catalyst A at 500° C. for 5 h, and calcined. | 7.04 | 6.13 | 175 | 0.139 |

*Percent P removed (with respect to initial P content before water treatment) calculated from P content of catalyst (B through G) and of catalyst A.

Example 5

Those catalysts (i.e. Catalysts B and E) that showed the greatest increase in activity and stability contained from about 5.4 to 5.6 wt % phosphorus by weight of catalyst. To provide a comparison, a phosphorus-treated ZSM-5 zeolite (Catalyst H) prepared in the same manner as Catalyst A in Table 1 but that contained only 5.3 wt % phosphorus and that was not treated with water was used in toluene methylation. Catalyst H showed significantly lower activity compared to the water-treated zeolite catalysts having similar amounts of phosphorus, as shown in FIG. 1.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.F

We claim:

1. A method of preparing a zeolite catalyst comprising:
treating a zeolite with a phosphorus compound prior to combining with any optional binder with the zeolite;
calcining the phosphorus-treated zeolite; and
contacting the calcined phosphorus-treated zeolite with liquid water by at least one of (1) immersing the calcined phosphorus-treated zeolite in liquid water and (2) contacting the calcined phosphorus-treated zeolite with flowing liquid water.

2. The method of claim 1, wherein:
the calcined phosphorus-treated zeolite is contacted with liquid water at a temperature of from about 25° C. to about 100° C.

3. The method of claim 1, wherein:
the zeolite is a ZSM-5 zeolite.

4. The method of claim 1, wherein:
the phosphorus-treated zeolite is bound with a binder material.

5. The method of claim 4, wherein:
the binder material is an aluminum-containing material.

6. The method of claim 1, wherein:
the phosphorus treated zeolite catalyst has a phosphorus content of from at least about 0.01 g P/g zeolite to about 0.15 g P/g zeolite prior to contacting the phosphorus-treated zeolite with liquid water.

7. The method of claim 1, wherein:
the zeolite has a silica/alumina mole ratio of at least about 250.

8. The method of claim 4, wherein:
the phosphorus-treated zeolite is bound and then contacted with liquid water.

9. The method of claim 5, wherein:
the phosphorus-treated zeolite is bound and then contacted with liquid water.

10. The method of claim 1, wherein:
the calcined phosphorus-treated zeolite is contacted with flowing liquid water, and wherein the flowing liquid water is carried in a gas diluent stream.

11. The method of claim 1, wherein:
treating the zeolite with a phosphorus compound comprises an aqueous phosphorus treatment.

12. The method of claim 11, wherein:
the phosphorus compound is at least one of phosphoric acid ($H_3PO_4$), phosphorus acid ($H_3PO_3$) and ammonium hydrogen phosphate (($NH_4$)$_2$$HPO_4$).

13. The method of claim 1, wherein:
the phosphorus treated zeolite catalyst is calcined at a temperature of at least about 300° C.

14. The method of claim 1, wherein:
the zeolite is a medium pore zeolite.

15. The method of claim 1, wherein:
phosphorus is removed from the calcined phosphorus-treated zeolite in an amount of from about 20% or more of the initial phosphorus content by contacting the calcined phosphorus-treated zeolite with liquid water.

16. The method of claim 15, wherein:
the amount of phosphorus removed is from about 20% to about 30% of the initial phosphorus content.

17. The method of claim 3, wherein:
the ZSM-5 zeolite has a silica/alumina molar ratio of at least about 250.

18. The method of claim 17, wherein:
the ZSM-5 zeolite is bound with a binder material after the ZSM-5 zeolite is treated with the phosphorus compound.

19. The method of claim 18, wherein:
phosphorus is removed from the calcined phosphorus-treated zeolite in an amount of from about 20% or more of the initial phosphorus content by contacting the calcined phosphorus-treated zeolite with liquid water.

20. A zeolite catalyst comprising a calcined phosphorus-treated zeolite having an initial phosphorus content that is reduced from about 20% to about 30% less of the initial phosphorus content by contacting the calcined phosphorus-treated zeolite with liquid water.

* * * * *